US007156820B2

(12) United States Patent
Polonchek

(10) Patent No.: US 7,156,820 B2
(45) **Date of Patent: *Jan. 2, 2007**

(54) EXTREMITY SUPPORT RACK

(76) Inventor: Jeanna S. Polonchek, 707 Crane Ave. South, Taunton, MA (US) 02780

( * ) Notice: Subject to any disclaimer, the term of this patent is extended or adjusted under 35 U.S.C. 154(b) by 179 days.

This patent is subject to a terminal disclaimer.

(21) Appl. No.: 10/832,956

(22) Filed: Apr. 27, 2004

(65) Prior Publication Data

US 2004/0204668 A1 Oct. 14, 2004

Related U.S. Application Data

(63) Continuation of application No. 10/254,149, filed on Sep. 25, 2002, now Pat. No. 6,764,458.

(51) Int. Cl.
*A61F 5/00* (2006.01)

(52) U.S. Cl. .......................... 602/32; 602/33; 128/845; 5/648

(58) Field of Classification Search .................. 602/16, 602/23, 32–33; 128/882, 845, 846; 5/648
See application file for complete search history.

(56) References Cited

U.S. PATENT DOCUMENTS

| | | | |
|---|---|---|---|
| 830,776 A | 9/1906 | Flagg | |
| 2,519,729 A | 8/1950 | Alexander | |
| 2,552,370 A | 5/1951 | Curtis | |
| 3,066,322 A | 12/1962 | Derby | |
| 3,753,557 A | 8/1973 | Kelley | |
| 3,817,512 A | 6/1974 | Torrey | |
| 3,931,654 A | 1/1976 | Spann | |
| 3,946,451 A | 3/1976 | Spann | |
| 4,146,140 A | 3/1979 | Suter et al. | |
| 4,180,254 A | 12/1979 | Lee et al. | |
| 4,327,714 A | 5/1982 | Spann | |
| 4,644,593 A | 2/1987 | O'Brien | |
| 4,866,796 A | 9/1989 | Robinson et al. | |
| 4,910,818 A | 3/1990 | Grabill et al. | |
| 5,046,487 A | 9/1991 | Scott | |
| 5,449,221 A | 9/1995 | Stander | |
| 6,764,458 B1 * | 7/2004 | Polonchek | 602/32 |

OTHER PUBLICATIONS

Clinical Bibliography—CPM, "SHOULDER", http://www.arthroscopy.com/sp06002.htm, Aug. 11, 2002.

EmployerHealth.com, "Employer Health Register, Directory of Products and Services, 'Continuous Passive Motion Devices (CPM)'", http://www.employerhealth.com/_sample_pages/dpscpm.htm, Aug. 11, 2002.

EmployerHealth.com, "Employer Health Register, Supplier Profile", http://www.employerhealth.com/_sample_pages/sp2979.htm, Aug. 11, 2002.

VQ OrthoCARE, "SHOULDER CPM", http://www.vqorthocare.com/cpm/shoulder.htm, Aug. 20, 2002.

Span+Aid Cast Elevator advertisement, Span-America, Inc. South Carolina, 1978.

(Continued)

*Primary Examiner*—Michael A. Brown
(74) *Attorney, Agent, or Firm*—Cesari and McKenna, LLP; Robert A. Cesari, Esq.

(57) ABSTRACT

A portable extremity support rack that offers a quick, easy, accessible and effective way to apply the standard RICE principle for post traumatic injury management. The extremity support rack collapses into a portable carrying case so it can be easily stored when not in use or quickly transported to different settings where injury management may take place. An upper surface and a lower surface in the extremity support rack are adjustably elevated and positioned to comfortably fit injured limbs of any shape and size.

20 Claims, 7 Drawing Sheets

OTHER PUBLICATIONS

AUTOFLEX II, Continuous Passive Motion, "The Comprehensive Answer to Post-Operative Therapy in the Hospital and at Home" Form #1103, Chattanooga Group, Inc.

Sutter CarePlan II, Expanded Services for the Outpatient advertisement, "SUTTER CPM 9000 Home Rehab System", Dec. 1992.

PRO-MED Products Catalog, pp. 30, 31, 46 and 47.

* cited by examiner

EXTREMITY SUPPORT RACK

CROSS-REFERENCE TO RELATED APPLICATIONS

The present application is a continuation of commonly assigned U.S. patent application Ser. No. 10/254,149, which was filed on Sep. 25, 2002, now U.S. Pat. No. 6,764,458, by Jeanna S. Polonchek for an Extremity Support Rack and is hereby incorporated by reference.

FIELD OF THE INVENTION

The present invention relates to a portable extremity support rack that is collapsible and can be readily deployed in different settings where injury and/or trauma management may take place.

BACKGROUND INFORMATION

Because acute injuries to limbs often occur at unpredictable times and in a wide range of settings, injury management for these injuries may be carried out in a variety of different places including, but not limited to, physical therapy clinics, hospital emergency rooms, athletic facility playing fields/sidelines, athletic training rooms, patient homes and hospital recovery rooms.

Typically, acute injuries to limbs are treated by applying the RICE methodology: Rest, Ice, Compression and Elevation. Due to the unpredictability of where and when the injuries occur, it is important for medical practitioners to have the capability to perform standard RICE treatment in a number of different environments. Therefore, there is a need for a lightweight, portable extremity support rack that is easily set up for appropriate limb elevations in a variety of settings where RICE treatment takes place.

Previous versions of portable support racks are bulky, rigid and not adjustable, or their range of adjustment precludes the racks' use in treating some injuries. Furthermore, portable support racks often do not have the capability of functioning in a wide range of environments.

SUMMARY OF THE INVENTION

As compared with prior art implementations, the present invention provides a portable extremity support rack with increased range of motion, adjustable in both length and angle, allowing it to comfortably fit injured limbs of different sizes, shapes and lengths. Specifically, the support rack can be used to elevate an injured leg by adjustably positioning two separate surfaces that respectively support portions of the upper and lower leg. Similarly, the rack may be used to elevate an upper extremity limb such as an arm.

The support rack supports an injured limb along two separate surfaces, e.g., upper and lower cradles, that are independently positioned relative to each other. By adjustment of the relative displacements and angles at which the two surfaces are positioned, the rack can support injured limbs in myriad elevated positions. For instance, when used to support an injured leg, the thigh rests on a proximal lower cradle and the calf rests on a distal upper cradle. Additionally, an end-rest supports the weight of the extremity's outermost end, such as a foot.

The lower cradle is secured at an arbitrary position on a pair of lower rails, and the upper cradle is secured on a pair of upper rails. Each upper rail in the support rack is pivotally hinged to a corresponding lower rail, and each lower rail is additionally hinged to a rigid base. The two lower rails are supported by a set of lower struts, and, similarly, a separate set of upper struts elevates the upper rails. Specifically, the upper and lower struts are each pivotally hinged to the base on one end and attached to the upper and lower cradles, respectively, on the other end.

Advantageously, the upper and lower struts are each extendable so that the lower cradle and upper cradle are independently positioned at different heights relative to the base. Thus, a wide range of elevations for an injured extremity can be realized by selecting different extensions for the lower struts and upper struts. Further, the angles of the upper and lower struts can be independently set since each strut is pivotally hinged to the base. In the preferred embodiment, the relative positions of the upper and lower struts along the base are also adjustable.

Preferably, the base is part of a portable carrying case, and the extremity support rack is collapsible into the case for ease of transport and storage.

BRIEF DESCRIPTION OF THE DRAWINGS

The above and further advantages of the invention may be better understood by referring to the following description in conjunction with the accompanying drawings in which like reference numerals indicate identically or functionally similar elements, of which.

DETAILED DESCRIPTION OF AN ILLUSTRATIVE EMBODIMENT

Figure 1:
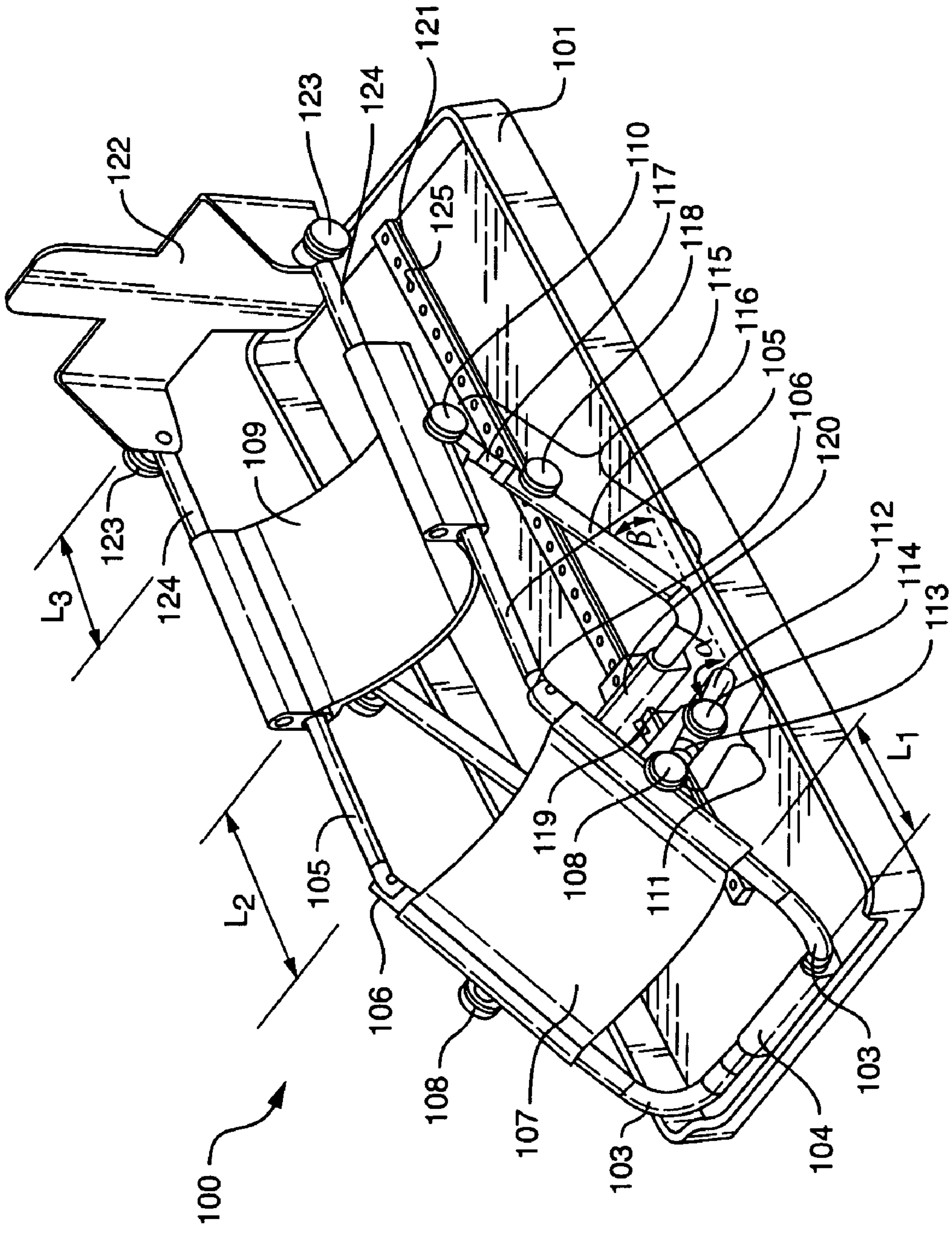
FIG. 1 is a side view of a support rack of the present invention.

As shown in FIG. 1, a portable extremity support rack 100 exemplifying the invention is mounted on a rigid base 101 of a portable carrying case. A pair of lower rails 103 are pivotally connected to the base at a hinge 104 and pivotally connected to a pair of upper rails 105 at hinges 106. A lower cradle 107 is positioned on the lower rails and secured by knobs 108. An upper cradle 109 is positioned on the upper rails and secured in place by knobs 110. The upper and lower cradles both have U-shaped cross-sections.

An end-rest surface 122 extends from the upper cradle to support an extremity's outermost end, such as a foot. When the rack is used to support an injured arm, the surface 122 may comprise a peg (not shown) that can be grasped by a hand. The end-rest surface is pivotally hinged to a pair of rail extensions 124 at hinges 123 to allow, e.g., a foot or ankle to be positioned at a desired angle. The rail extensions telescope into the upper cradle as illustrated.

A pair of lower struts 111, that support the lower cradle, are pivotally mounted on the base 101 on one end and attached to the lower cradle at the other end. More specifically, the lower struts are pivotally attached to a bracket 119 that rests on a track 121 attached to the base. Each lower strut comprises a lower portion 112, connected to the bracket 119, and an extension portion 113 that telescopes into portion 112 and attaches to the lower cradle. The strut portions are held in position by a clamp (not shown) controlled by a knob 114. The bracket 119 is adjustably positioned along the track by setting a pin (not shown) into one of the holes 125 in the track.

Figure 2:
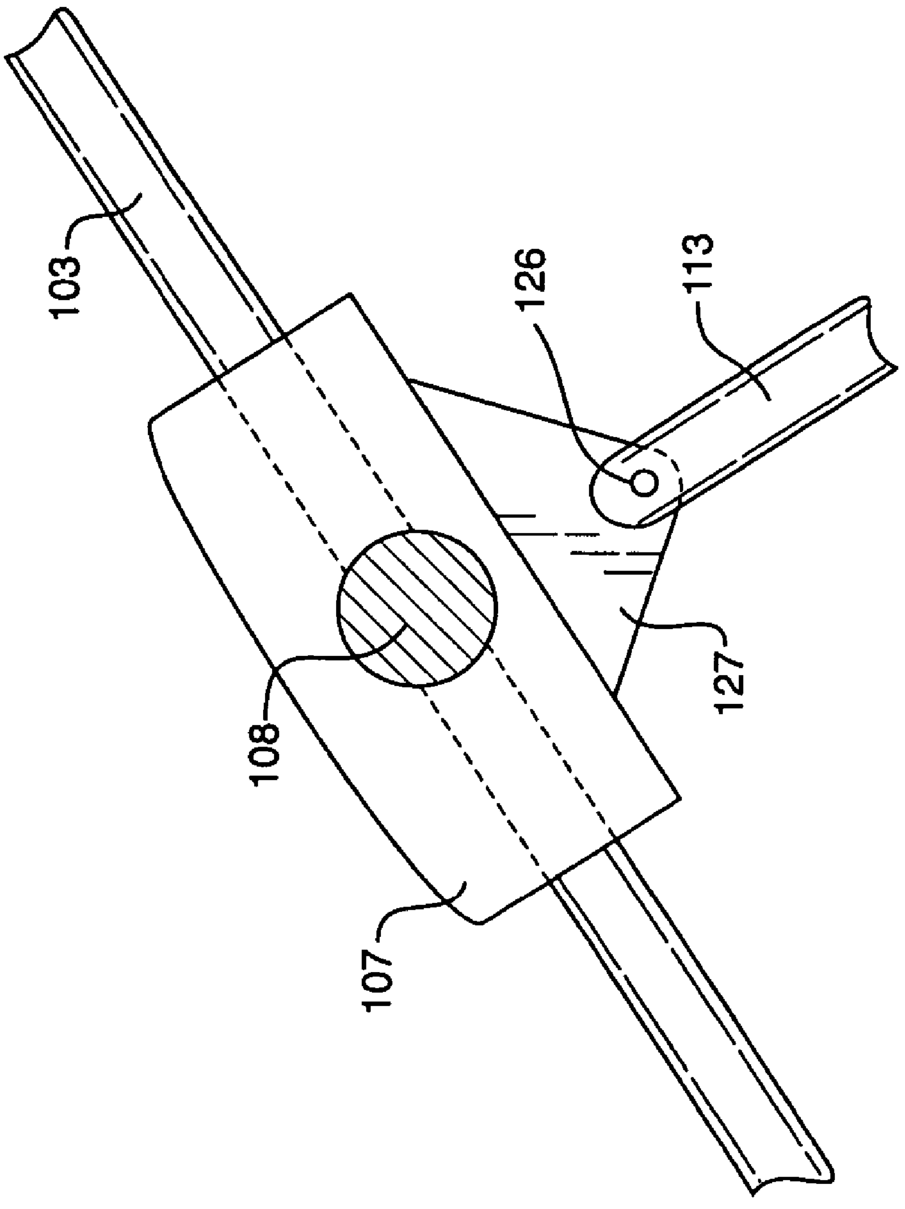
FIG. 2 is a side view of a lower cradle in the support rack.
Figure 3:
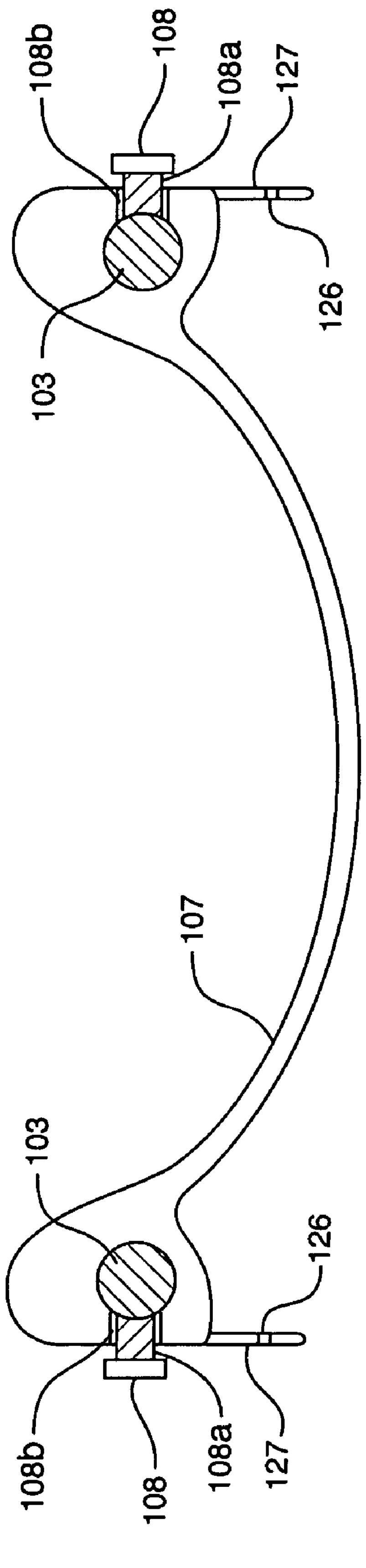
FIG. 3 is a cross-sectional view of the lower cradle of FIG. 2.

As shown in FIGS. 2 and 3, the outer end of each extension portion 113 is pivotally connected by a hinge pin 126 to a flange 127 attached to the lower cradle. The knobs 108 on each side of the lower cradle are attached to bolts 108*a* that are threaded through inserts 108*b* in the lower cradle. Thus, rotation of the knobs applies clamping forces on the lower rails 103, thereby securing the position of the cradle on the rails.

Referring again to FIG. 1, a pair of upper struts 115, that support the upper cradle, are pivotally mounted on the base 101 on one end and attached to the upper cradle at the other end. More specifically, the upper struts are pivotally attached to a bracket 120 that rests on track 121 attached to the base. Each upper strut comprises a lower portion 116, connected to the bracket 120, and an extension portion 117 that telescopes into portion 116 and attaches to the upper cradle. The strut portions are held in position by a clamp (not shown) controlled by a knob 1.18. The bracket 120 is adjustably positioned along the track by setting a pin (not shown) into one of the holes 125 in the track.

Figure 4:
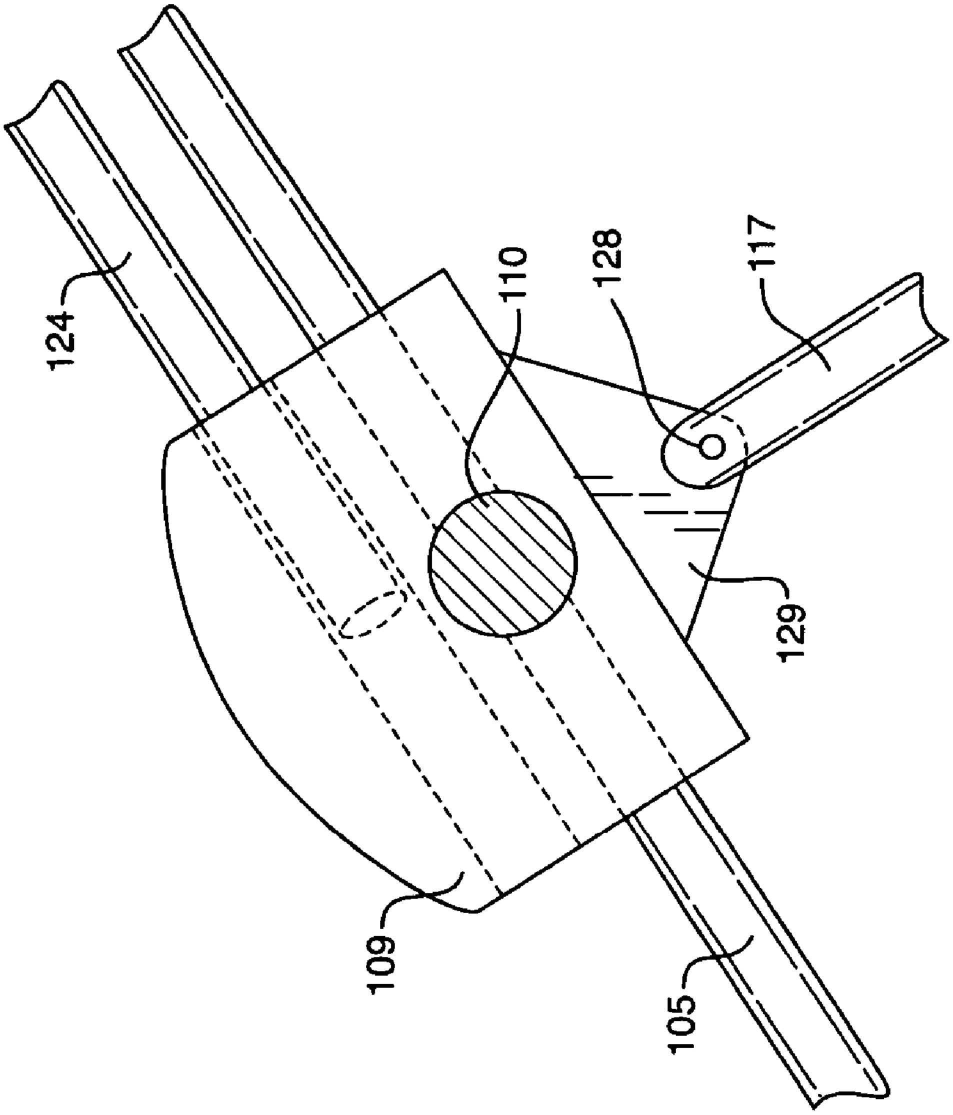
FIG. 4 is a side view of an upper cradle in the support rack.
Figure 5:
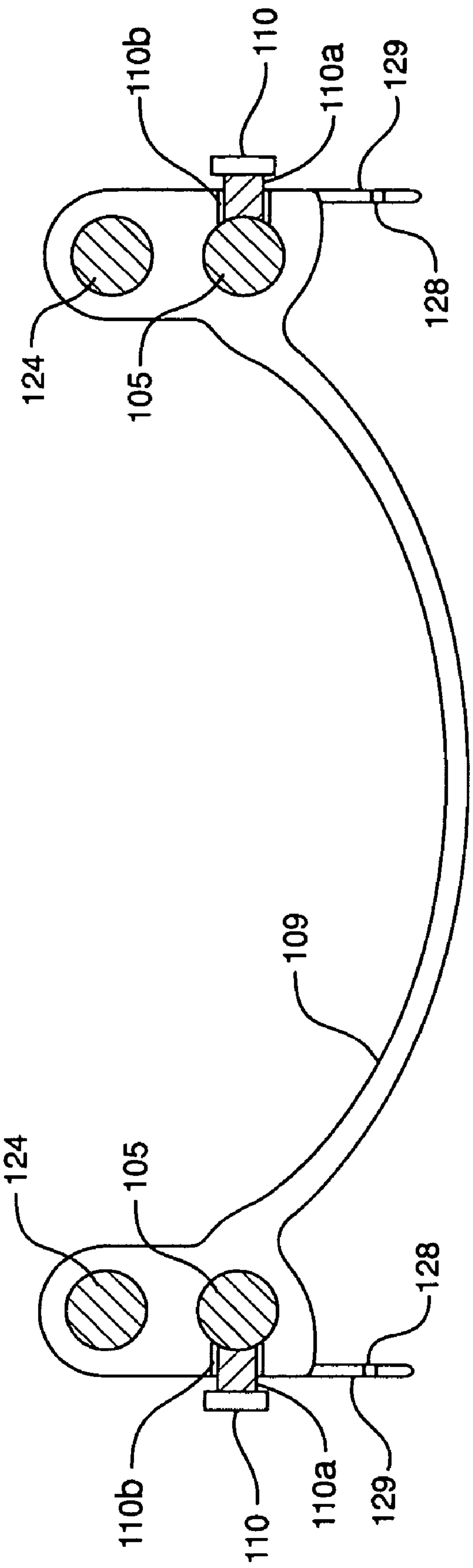
FIG. 5 is a cross-sectional view of the upper cradle of FIG. 4.

As shown in FIGS. 4 and 5, the outer end of each extension portion 117 is pivotally connected by a hinge pin 128 to a flange 129 attached to the upper cradle. The knobs 110 on each side of the upper cradle are attached to bolts 10*a* that are threaded through inserts 110*b* in the upper cradle. Thus, rotation of the knobs applies clamping forces on the upper rails 105, thereby securing the position of the cradle on the rails.

Figure 6:
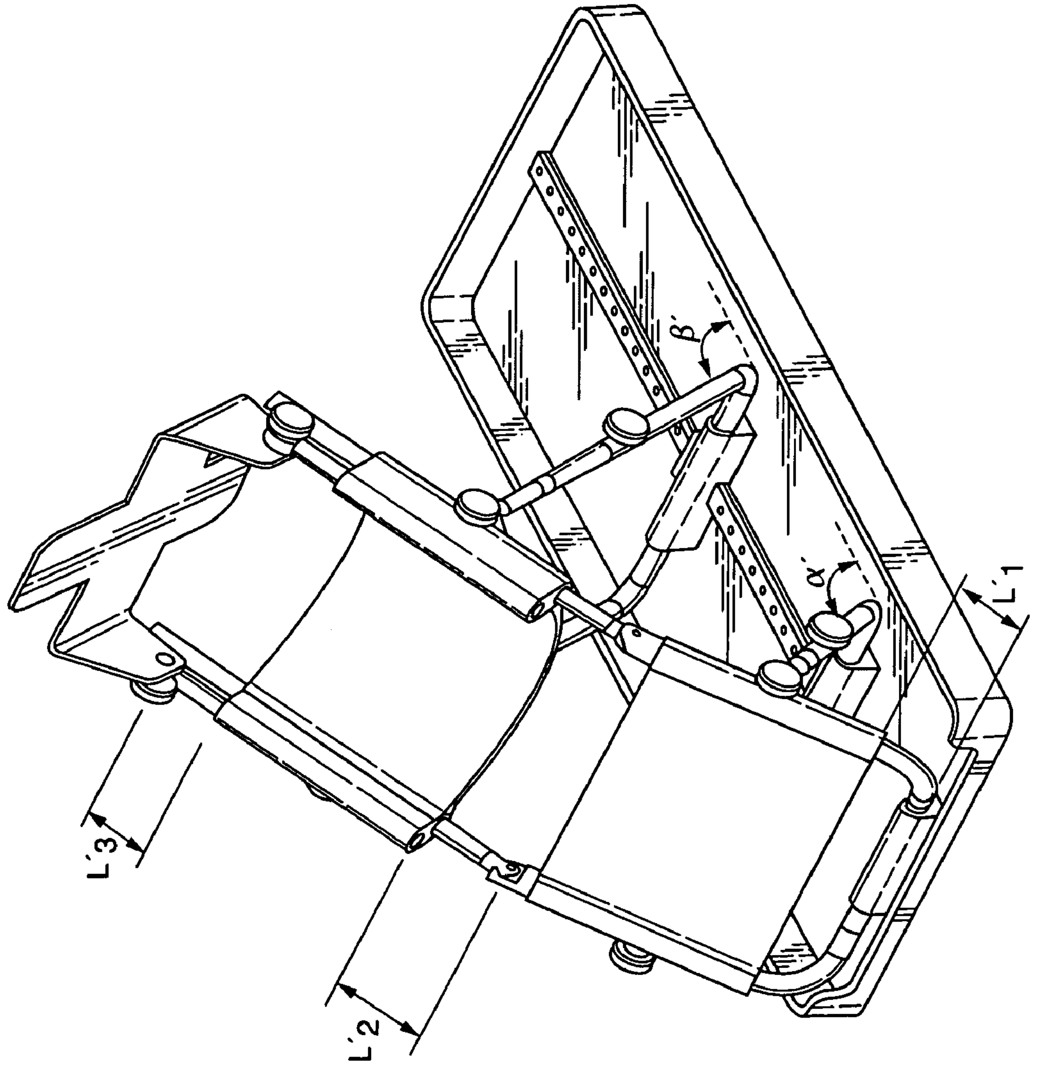
FIG. 6 is a side view of the support rack of FIG. 1 adjusted to an arbitrary position.

FIGS. 1 and 6 illustrate the capability of the support rack to assume an almost unlimited variety of positions. As shown in FIG. 1, the lower cradle 107 is located a distance $L_1$ from hinge 104, the upper cradle 109 is located a distance $L_2$ from hinge 106 and the end-rest surface 122 is located a distance $L_3$ from the upper cradle. Further, the lower struts are set at an angle $\alpha$ relative to the base and the upper struts are set at an angle $\beta$. In FIG. 6, the lower and upper struts are set at different angles, $\alpha'$ and $\beta'$, relative to the base. Similarly, the upper and lower cradles and end-rest support are located in different positions than in FIG. 1, as shown by $L_1'$, $L_2'$ and $L_3'$. Additionally, the positions of brackets 119 and 120 along the track 121 differ in FIGS. 1 and 6.

Figure 7:
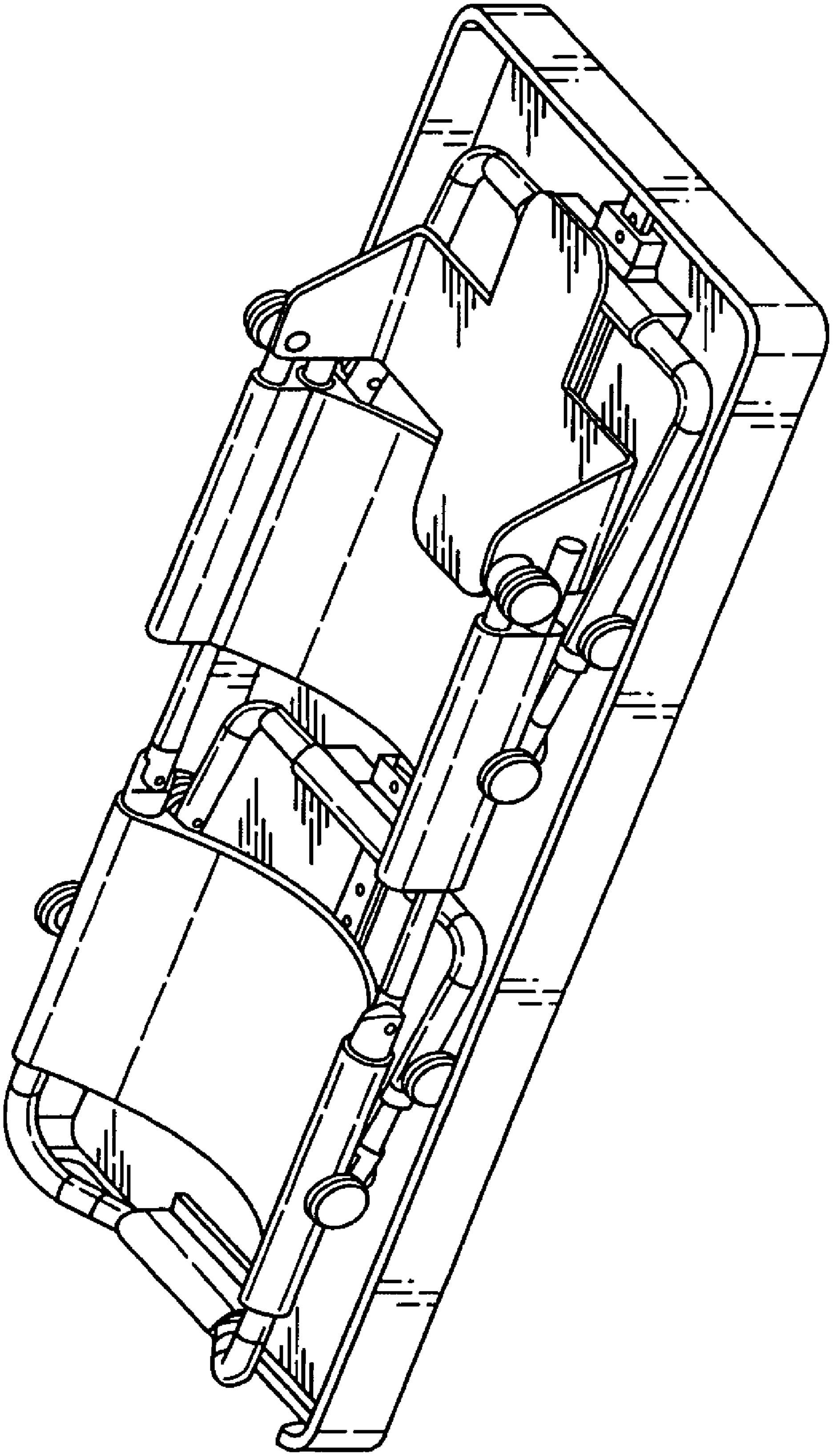
FIG. 7 is a top view of the support rack of FIG. 1, collapsed into a portable carrying case.

FIG. 7 illustrates the portable extremity support rack of FIG. 1 collapsed into a portable carrying case. The rack in its folded position is ideal for transport and/or storage.

Various modifications and additions can be made without departing from the spirit and scope of the invention. For example, at least one end of the base may be supported by one or more telescoping struts (not shown) that can adjustably incline the plane of the base. The base may additionally include panels (not shown) that telescope from its sides to increase the width of the base. Further, the base need not be mounted on the bottom of a carrying case, as shown in the illustrative embodiment. Instead, the base may be attached to the top or a side of the case, or, alternatively, may be portable independent of a carrying case.

It is expressly contemplated to pivotally hinge the upper and lower struts at fixed positions on the base and adjust their relative angles by adjustably attaching them to their respective cradles. Additionally, in lieu of the brackets described herein, the lower and upper struts may attach to the track using other known methods, such as clamping mechanisms. Further, those skilled in the art will understand that the clamps used as securing mechanisms in the present invention may be implemented with other equivalent mechanisms known in the art; e.g., setting a pin in one of a plurality of holes. Although U-shaped cross-sections are shown for the upper and lower cradles, their respective cross-sections may be tailored for extremities of different sizes and shapes. The cradles may be padded for extra comfort, e.g., with wool, foam, cloth, etc. Similarly, the end-rest surface may also be molded and/or padded. For example, the end-rest may be shaped as an oversized glove when the rack is used to support an injured arm. Also, one or more straps (not shown) may be attached to, e.g., the end-support, to provide added stability for an injured limb supported on the rack herein.

It will be understood by those skilled in the art that adjustment of the cradles, struts, brackets, rail extensions, etc. may be motorized to allow for passive range of motion. For example, the support rack may be adapted to provide continuous passive motion (CPM), e.g., by attaching motorized hydraulic pistons or jack screws to the struts. In addition, it is expressly contemplated that each strut supporting the upper and lower cradles may be independently adjustable. Therefore, by setting the struts supporting each side of a cradle to different lengths, the cradle may effectively be rotated clockwise or counter-clockwise to accommodate various shaped limbs. Accordingly this description is meant to be taken only by way of example and not to otherwise limit the scope of the invention.

What is claimed is:

1. A portable extremity support rack comprising:

a generally planar base;

a set of lower rails, each lower rail being pivotally connected at one end to the base;

a set of upper rails, each upper rail being pivotally connected at one end to a corresponding lower rail;

a lower cradle adjustably positioned on one or more of the lower rails;

an upper cradle adjustably positioned on one or more of the upper rails;

a set of extendable lower struts, each lower strut being pivotally connected at a first end to the base and attached at a second end to the lower cradle; and a set of extendable upper struts, each upper strut being pivotally connected at a first end to the base and attached at a second end to the upper cradle, whereby the angular orientations of the rails and the struts are adjustable by rotating them in a plane perpendicular to the base.

2. The support rack of claim 1, wherein at least some of the upper and lower struts are attached to fixed positions on the base.

3. The support rack of claim 1, wherein at least some of the upper and lower struts are adjustably attached to the base.

4. The support rack of claim 3, wherein the struts adjustably attached to the base are adjustably attached to a track attached to the base.

5. The support rack of claim 1, wherein at least one of the upper and lower cradles is padded.

6. The support rack of claim 5, wherein the padding includes foam.

7. The support rack of claim 5, wherein the padding includes cloth.

8. The support rack of claim 5, wherein the padding includes wool.

9. The support rack of claim 1, wherein at least one of the upper and lower cradles has a U-shaped cross-section.

10. The support rack of claim 1, wherein at least two of the extendable lower struts are extended different lengths so as to rotate the lower cradle with respect to the plane of the base.

11. The support rack of claim 1, wherein at least two of the extendable upper struts are extended different lengths so as to rotate the upper cradle with respect to the plane of the base.

12. The support rack of claim 1, wherein the base is supported by one or more telescoping struts that adjustably incline the plane of the base.

13. The support rack of claim 1, wherein the base includes one or more panels that telescope from the sides of the base, thereby increasing the width of the base.

14. The support rack of claim 1, further comprising a strap used to stabilize a limb supported on the support rack.

15. The support rack of claim 14, wherein the strap is attached to one of the upper and lower cradles.

16. The support rack of claim 1, wherein the support rack is attached to a surface of a carrying case.

17. The support rack of claim 1, wherein adjustments of at least one of the upper and lower struts is motorized.

18. The support rack of claim 1, wherein adjustments of at least one of the upper and lower cradles is motorized.

19. The support rack of claim 1, further comprising:

rail extensions oriented in the direction of the upper rails, each rail extension being attached to the upper cradle; and an end-rest pivotally hinged to the rail extensions, whereby the angular orientation of the end-rest is adjustable by rotations in a plane perpendicular to the base.

20. The support rack of claim 19, wherein the rail extensions are extendable from the upper cradle.

* * * * *